United States Patent [19]
Iwata et al.

[11] Patent Number: 6,011,618
[45] Date of Patent: Jan. 4, 2000

[54] METHOD AND APPARATUS OF SURFACE INSPECTION OF A DISK

[75] Inventors: Tetsuya Iwata; Shigeru Tsuchida, both of Nagaoka, Japan

[73] Assignee: System Seiko Co., Ltd., Niigata, Japan

[21] Appl. No.: 09/215,496

[22] Filed: Dec. 18, 1998

[30] Foreign Application Priority Data

Dec. 25, 1997 [JP] Japan .................................. 9-356770

[51] Int. Cl.[7] .................................................. G01N 21/00
[52] U.S. Cl. ........................ 356/237.2; 356/430; 356/448
[58] Field of Search ................................ 356/237.2, 430, 356/448, 431

[56] References Cited

U.S. PATENT DOCUMENTS 4,794,264  12/1988  Quackenbos et al. .
4,794,265  12/1988  Quackenbos et al. .
5,389,794   2/1995  Allen et al. .

FOREIGN PATENT DOCUMENTS

8-122266   5/1996  Japan .............................. G01N 21/88
10-227744  8/1998  Japan .............................. G01N 21/88

*Primary Examiner*—Robert H. Kim
*Assistant Examiner*—Reginald A. Ratliff
*Attorney, Agent, or Firm*—McCormick, Paulding & Huber LLP

[57] ABSTRACT

An apparatus for inspecting a surface of a disk comprises an indexing table having chucks for holding said disks respectively, said chucks being arranged angularly at regular intervals on the indexing table. Each of disks held by the respective chucks is moved by indexing revolution of the indexing table sequentially from a loading station where the disk is loaded onto the chuck, to an inspection station where the disk is inspected for a surface of the disk and then to an unloading station where the inspected disk is unloaded to the outside of the apparatus. The disk loaded onto a chuck at the loading station is driven to rotate until the disk gets to a predetermined rate of revolution before the disk arrives at the inspection station. The disk which has already get to the predetermined rate of revolution can be immediately inspected for the surface of the disk in the inspection station by an inspection device.

11 Claims, 10 Drawing Sheets

T2: time for getting to a predetermined rate of revolution

T4: inspection time

T5: time for getting to rate of revolution zero

Fig. 10

METHOD AND APPARATUS OF SURFACE INSPECTION OF A DISK

BACKGROUND OF THE INVENTION

1. Field of the Invention

This invention generally relates to a technology of surface inspection of a magnetic disk to be used as storage medium of computers after the completion of a series of predetermined surface treatment steps in the process of manufacturing the disk.

2. Related Art Statement

Magnetic disks to be used as storage medium of computers are typically made of aluminum alloy or glass and have a central through hole therein and a magnetic film formed on the surface thereof.

For preparing a disk from aluminum alloy, it is typically punched out of a plate of aluminum alloy by means of a press to show predetermined inner and outer diameters and then subjected to a series of surface treatment steps including grinding, lapping and polishing, after which the surface of the disk is inspected to see if it meets given precision requirements.

In order to continuously and efficiently inspect disks in known arrangements for manufacturing disks on a mass production system, disks are rotatably held on an indexing table, namely an indexing rotary table adapted to revolve by a predetermined indexing angle and move the discs in turn to a loading station where one or more than one disks are loaded on the indexing table, to an inspection station where the disks are inspected for the surface, and then to an unloading station where the disks which have been inspected are unloaded from the indexing table and delivered to the outside. The indexing table is provided with chucks arranged angularly at a predetermined regular pitch for holding disks.

Since a magnetic disk is prepared by laying a magnetic film on the opposite surfaces of a blank disk, it is normally turned upside down on a same indexing table so that the two surfaces may be inspected on the same table. Alternatively, a pair of indexing tables may be used so that each magnetic disk is inspected on one of the tables for one side thereof and then moved onto the other table, where it is inspected for the other side.

With either system, spot light such as laser spot light is made to strike the disk which has been moved to the inspection station by the indexing table and the reflected light is used to inspect the disk for the surface and find out if the surface is damaged or not and if foreign matters such as dirt is adhering to the surface or not. More specifically, the disk is driven to rotate so that it maybe scanned radially by spot light to inspect the entire surface.

In an attempt to inspect the disk efficiently within a short time, the disk held by a chuck is caused to revolve typically at a rate of about 6,000 rpm by the chuck during the inspection. With such a high rate of revolution, the surface of each disk can be inspected in about seven seconds.

However, with the above described arrangement for examining a disk for the surface, the chuck is made to pass through the central through hole of the disk and rigidly hold the disk. Then, care should be taken not to tighten the chuck too hard in order to prevent the peripheral surface of the central through hole from being damaged by the chuck. Therefore, a problem of relative displacement between the disk and the chuck can arise due to the relatively loose chuck when the disk on the inspection station that is initially not revolving is driven to get to a predetermined high rate of revolution within a very short period of time. This problem is currently avoided by taking a predetermined time for an initially not revolving disk to get to the predetermined rate of revolution for inspection and, conversely, for a disk revolving at a predetermined high rate of revolution to get to a complete halt after the end of inspection.

Thus, conventionally, after getting to the inspection station on a indexing table, the disk to be inspected on the indexing table is driven to rotate until it gets to a predetermined rate of revolution, when an operation of inspecting the disk starts. With such an arrangement, the total time requirement will be the sum of the time required for the proper inspection of the disk and the time necessary for the disk to get to a predetermined rate of revolution at the inspection station.

SUMMARY OF THE INVENTION

Therefore, it is an object of the present invention to provide a method for inspecting the surface of a disk quickly within a short time.

Another object of the invention is to provide an apparatus for inspecting a disk, wherein said apparatus comprises an indexing table having chucks arranged angularly at regular intervals to hold respective disks and adapted to revolve in order to move the disks sequentially from a loading station to an inspection station.

Still another object of the invention is to provide an apparatus for inspecting a disk, wherein said apparatus is adapted to start inspecting a disk immediately when the disk is brought to an inspection station.

A further object of the invention is to provide an apparatus for inspecting a disk, wherein said apparatus comprises a first indexing table adapted for indexing revolution in order to move a disk to an inspection station for inspecting one of the surfaces of the disk and a second indexing table also adapted for indexing revolution in order to move the disk to another inspection station for inspecting the other surface of the disk.

According to an aspect of the invention, there is provided a method of surface inspection of a disk adapted to move a disk from a loading station to an inspection station and then to an unloading station by indexing revolution of an indexing table having a number of chucks arranged angularly at regular intervals for respectively receiving disks by means of their through holes and holding them in mutual engagement in order to inspect the surface of said disk, said method comprising: a loading step for loading said disk onto the chuck positioned at the loading station; a first transfer step for transferring said disk from the loading station to the inspection station by rotating the indexing table; an inspection step for inspecting the surface of said disk moved to the inspection station while driving the disk to rotate at a predetermined rate of revolution; a second transfer step for transferring said disk from said inspection station to said unloading station after the end of inspection; and a start-up step for driving said disk to start revolving after having loaded said disk onto said chuck at the loading station and before arriving at said inspection station, thereby inspecting the surface of said disk brought to the inspection station while revolving.

Preferably, said disk is made to get to said rate of revolution for inspection in said start-up step before said disk arrives at said inspection station from said loading station.

Preferably, said disk is made to get to said rate of revolution for inspection in said start-up step before it arrives at said inspection station from said loading station and transferred to said inspection station while maintaining said rate of revolution for inspection after getting to said rate of revolution.

According to another aspect of the invention, there is provided an apparatus of surface inspection of a disk having a central through hole, said apparatus comprising an indexing table having a number of chucks arranged angularly at regular intervals for respectively receiving disks by passing through said through holes and holding them, said index table being and adapted to be driven to rotate for indexing revolution in order to move the disk from a loading station to an inspection station and then to an unloading station; rotary drive means fitted to said indexing table for driving said chucks to rotate; loading means for loading an uninspected disk onto the chuck positioned at the loading station; surface inspection means for inspecting a surface of said disk transferred from said loading station to the inspection station; unloading means for unloading the disk transferred from said inspection station to said unloading station after end of inspection; and control means for driving said disk to start revolving before said disk loaded onto said chuck arrives at said inspection station from said at the loading station, thereby inspecting the surface of said disk brought to the inspection station while revolving.

Preferably, said control means causes said disk to get to said rate of revolution for inspection before it arrives at said inspection station from said loading station.

Preferably, said control means cause said disk to get to said rate of revolution for inspection before said disk arrives at said inspection station from said loading station and said disk got to said rate of revolution is transferred to said inspection station while maintaining said rate of revolution for inspection.

Preferably, said indexing table has a plurality of loading stations, a plurality of inspection stations and a plurality of unloading stations, thereby transferring and inspecting the surfaces of a plurality of disks simultaneously.

Still preferably, a disk positioned at the loading station is transferred to the inspection station by an indexing rotary motion of said indexing table with an angle of 120° and then to the unloading station by further indexing rotary motion of said indexing table with an angle of 120°.

An apparatus of surface inspection of a disk according to the invention may comprise a pair of indexing tables provided adjacent to each other and inverting means for inverting said disk arranged between said pair of indexing tables, thereby inspecting one of the opposite surfaces of said disk on one of said indexing tables and the other surface on the other indexing table.

An apparatus of surface inspection of a disk according to the invention may further comprise inverting means for inverting said disk held to said chuck, thereby inspecting the opposite surfaces of said disk by means of said single indexing table adapted for indexing revolution.

An apparatus of surface inspection of a disk according to the invention may have a first loading station for loading an unprocessed disk having its opposite surfaces still uninspected, a first inspection station for inspecting one of the surfaces of the disk, an inverting station for releasing the disk having one of its surfaces inspected, a second loading station for loading said released and inverted disk, a second inspection station for inspecting the other surface of said disk, an unloading station for delivering said disk having its opposite surfaces inspected to the outside, and a total of six chucks provided on the indexing table corresponding to said six stations respectively.

Thus, according to the invention, a disk brought to the inspection station for inspecting the surface thereof has been revolving so that the operation of inspecting the surface at the inspection station can start quickly to improve the efficiency of inspection.

Additionally, the time period to be spent for loading a disk at the loading station and moving it to the inspection station can be used for the operation of driving a disk received by a chuck by means of the central through hole of the disk and held in engagement with the chuck to rotate and of making it get to a predetermined rate of revolution so that the operation of making the disk to get to a predetermined rate of revolution can take time sufficient to eliminate any undesired relative displacement of the disk and the chuck.

Other objects and other novel features of the present invention will become apparent through the following description made by referring to the accompanying drawings.

DESCRIPTION OF THE PREFERRED EMBODIMENTS

Figure 1:
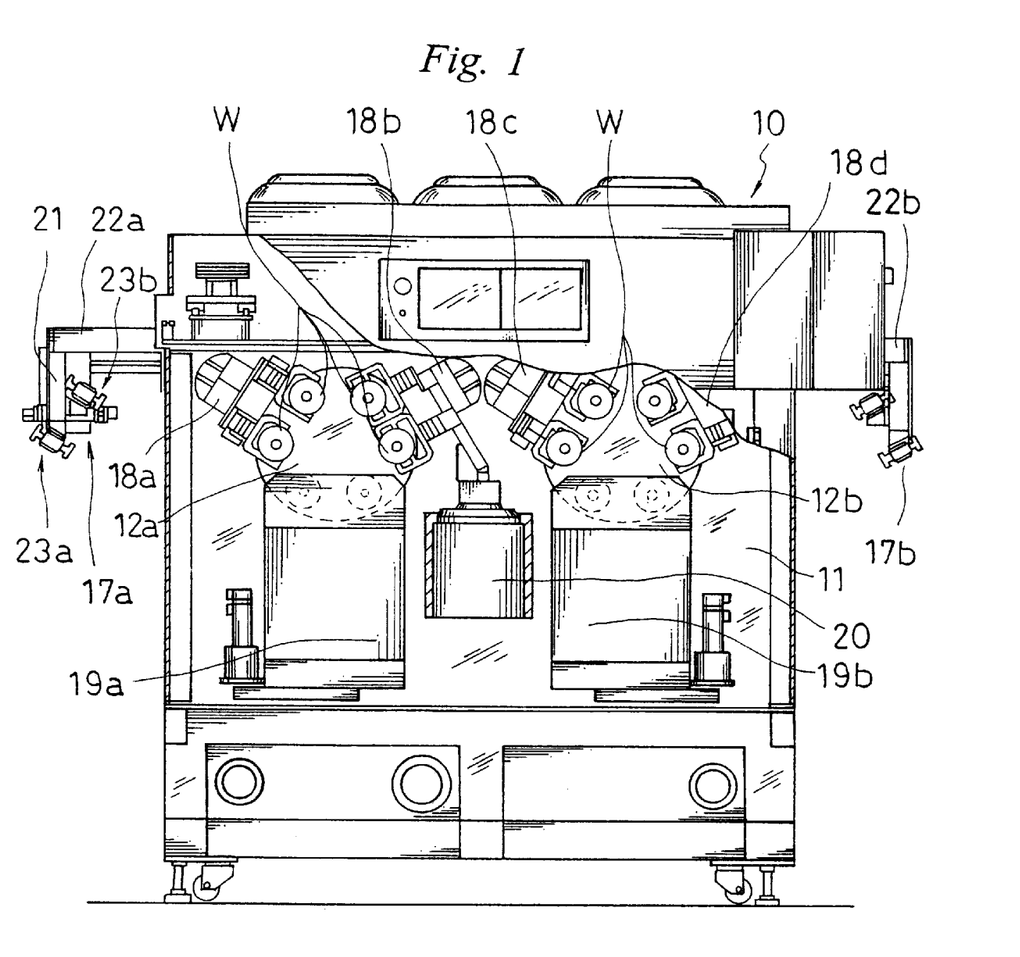
FIG. 1 is a schematic front view of an embodiment of surface inspection apparatus according to the invention.

Referring to FIG. 1, an apparatus for surface inspection of a disk according to the invention comprises a housing 10 containing therein a vertical support panel 11, to which a pair of indexing tables 12a, 12b are rotatably secured with their axes of rotation running horizontally.

Figure 2:
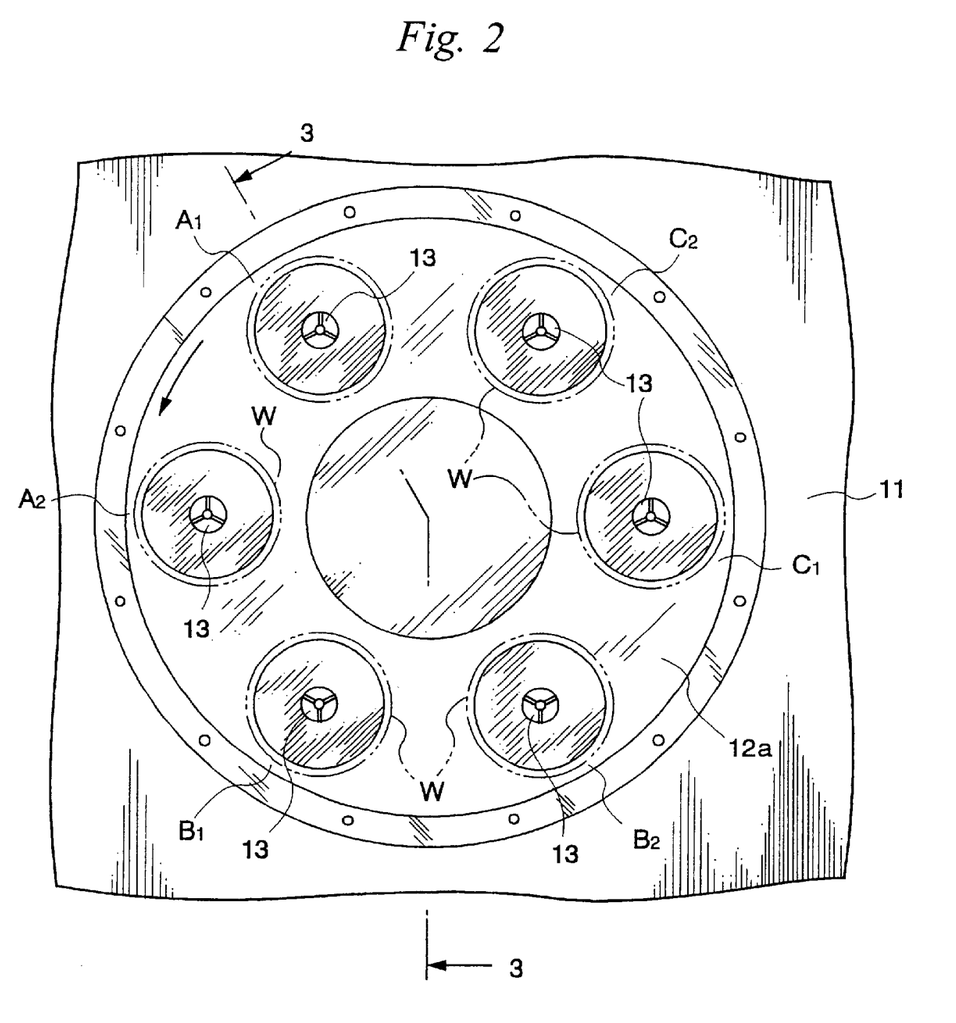
FIG. 2 is a schematic enlarged front view of the indexing table of FIG. 1.
Figure 3:
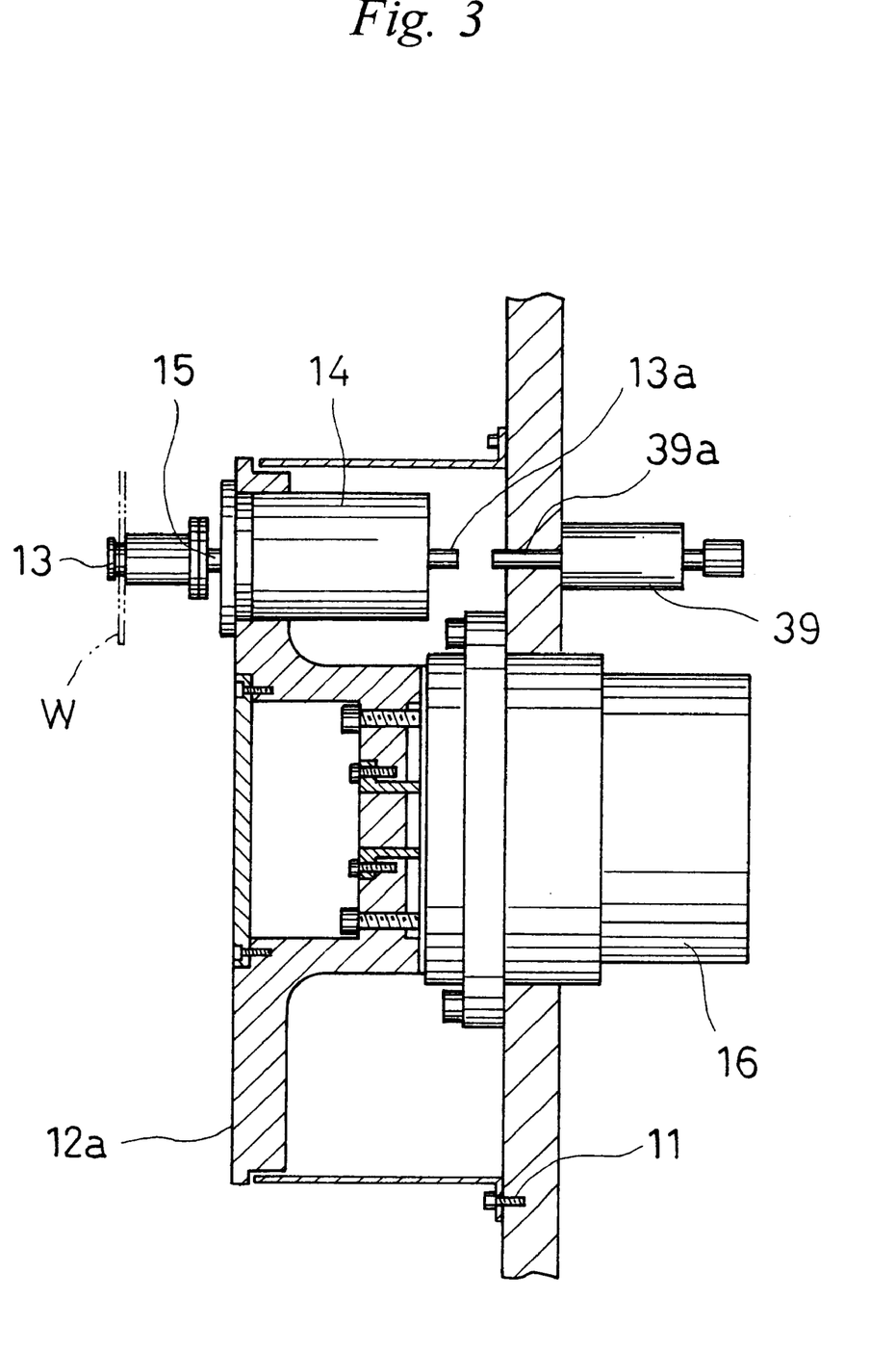
FIG. 3 is a schematic cross sectional view taken along line 3—3 in FIG. 2.

FIG. 2 is an enlarged view of one of the indexing tables, or the indexing table 12a. FIG. 3 is a cross sectional view of the table of FIG. 2. As shown in FIGS. 2 and 3, the indexing table 12a carries thereon a total of six collets type chucks 13 arranged angularly at regular intervals of 60° along its circumference, and each of the chucks 13 is fitted to a spindle 15 of a motor 14. Thus, the chuck 13 is driven to rotate by the motor 14. While only a single motor 14 is shown in FIG. 3, it will be appreciated that the six chucks 13 in FIG. 2 are connected to and driven by respective motors (not shown) which are identical relative to each other. Each chuck 13 is adapted to receive a disk W as the chuck 13 is made to pass through a central hole of the disk W so that each of the chuck 13 engagedly hold the disk W, which is in fact a disk substrate for a magnetic disk to be prepared from it. Note that the respective disks W are indicated by dotted broken lines in FIG. 2.

Referring to FIG. 3, the indexing table 12a is driven to rotate by a motor 16 secured to the support panel 11 by every 120°.

Referring to FIG. 2, the indexing table 12a carries thereon a total of six chucks 13 so that the single indexing table 12a can hold up to six disks W by way of the chucks 13. In the illustrated embodiment, the indexing table 12a is driven to rotate counterclockwise as shown in FIG. 2 by an arrow, and move a disk W from loading station A1 located at the left upper corner in FIG. 2 to inspection station B1 angularly and forwardly displaced from the loading station A1 by 120° and then to unloading station C1 angularly and forwardly displaced from the inspection station B1 also by 120°. Another set of loading station A2, inspection station B2 and unloading station C2 are arranged on the indexing table 12a for a second disk W at positions angularly and forwardly displaced by 60° from the loading station A1, the inspection station B1 and the unloading station C1 respectively so that the second disk W is also moved to the respective stations in series by the indexing revolution of the indexing table 12a.

Therefore, with the illustrated embodiment, a pair of disks W are loaded simultaneously onto the respective chucks 13 of the loading stations A1 and A2, inspected simultaneously at the respective inspection stations B1 and B2 and then unloaded simultaneously at the respective unloading stations C1 and C2.

The other indexing table 12b has a configuration similar to that of the indexing table 12a so that the disks W, which have been held to the indexing table 12a and inspected for one of the opposite surfaces, are turned upside down and held onto the indexing table 12b, where the disks W are to be inspected for the other surface.

Referring back to FIG. 1, the housing 10 is provided with a transfer hand 17a for feeding a pair of disks W into the housing 10 and also with a setter hand 18a fitted to the support panel 11 at a position adjacent to the loading stations of the indexing table 12 for receiving the pair of disks W from the transfer hand 17a and passing it to the indexing table 12a. The disks W are loaded onto the respective chucks 13 at the loading stations A1 and A2 for inspection by the transfer hand 17a and the setter hand 18a.

The disks W held by the respective chucks 13 at the loading stations A1, A2 are then moved to the respective inspection stations B1, B2 as the indexing table 12a is rotated by 120° for indexing revolution. An inspection device 19a is arranged at the inspection stations B1, B2 for inspecting one of the opposite surfaces of each of the disks W.

In the inspection device 19a, laser spot light is made to strike each of the disks W and the reflected light is used to inspect the disk W for the surface and find out whether the surface is damaged or not and whether foreign matters such as dirt is adhering to the surface or not. More specifically, the disks W may be scanned radially by laser spot light to inspect the surface while the disk W is being rotated at a predetermined rate of revolution.

When the inspection is over, the indexing table 12a is rotated by further 120° to move the disks W to the respective unloading stations C1, C2. The housing 10 is provided in the inside with another setter hand 18b similar to the setter hand 18a at a position corresponding to the unloading stations C1, C2.

As in the case of the indexing table 12a, a pair of setter hands 18c, 18d and an inspection device 19b are arranged along the circumference of the other indexing table 12b. An inverter hand 20 is arranged between the two indexing tables 12a, 12b for turning upside down the disks W. Therefore, the disks W brought respectively to the unloading stations C1, C2 by the indexing table 12a are passed onto the inverter hand 20 by way of the setter hand 18b and then loaded onto the respective chucks 13 at the loading stations A1, A2 of the indexing table 12b from the inverter hand 20 by way of the setter hand 18c. Thus, the setter hand 18b and the inverter hand 20 moves the disks W located at the unloading stations of the indexing table 12a out of them, and then the setter hand 18c loads them onto the respective chucks 13 of the loading stations A1, A2 of the indexing table 12b.

In the embodiment of FIG. 1, the setter hand 18b is arranged right behind the inverter hand 20 and therefore shown only partly there.

The disks W which have been inspected for the both opposite surfaces are then moved out of the housing 10 from the unloading stations C1, C2 of the indexing table 12b by means of the setter hand 18d and another transfer hand 17b. Thus, the setter hand 18d and the transfer hand 17b moves the disks W located at the unloading stations C1, C2 of the indexing table 12b out of them.

Figures 4A, 4B:
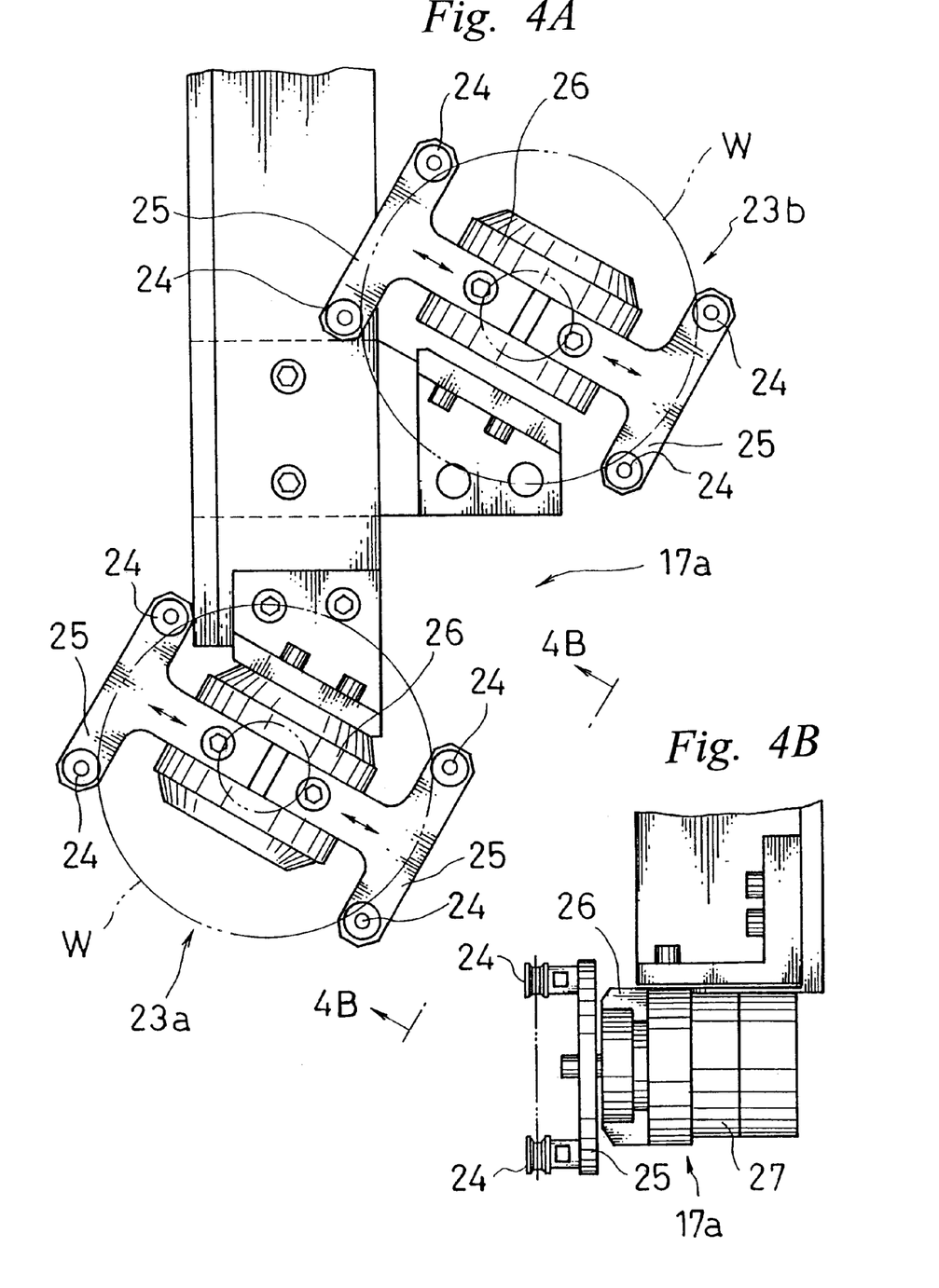
FIG. 4A is a schematic enlarged front view of the transfer hand of FIG. 1.
FIG. 4B is a schematic side view as viewed along arrows 4B—4B in FIG. 4A.

As seen from FIG. 1, the transfer hand 17a is movable vertically by means of a transfer lifter 21 and also horizontally by means of a guide member 22a. FIGS. 4A and 4B are enlarged views of the transfer hand 17a having a pair of fingers 23a, 23b for holding respectively a pair of disks W at the outer periphery thereof. Each of the fingers 23a, 23b has a pair of reciprocating members 25, each provided with a pair of rollers 24, which members 25 are adapted to move closer to and away from each other along a guide member 26 as shown by arrows. The transfer hand 17a is also provided with a pneumatic actuator 27 for driving the reciprocating members 25 to linearly move back and forth.

Figure 5:
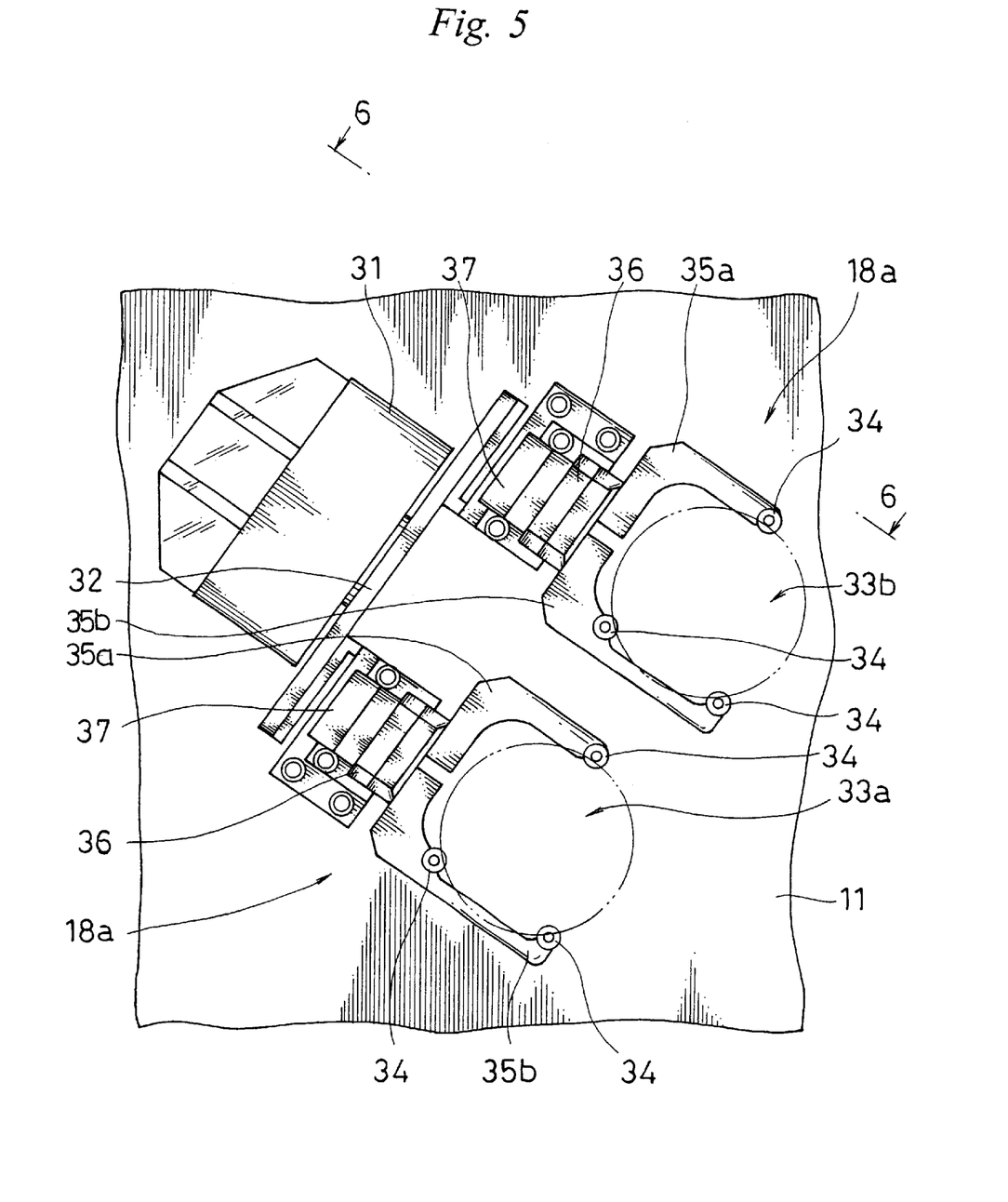
FIG. 5 is a schematic enlarged front view of the setting hand of FIG. 1.
Figure 6:
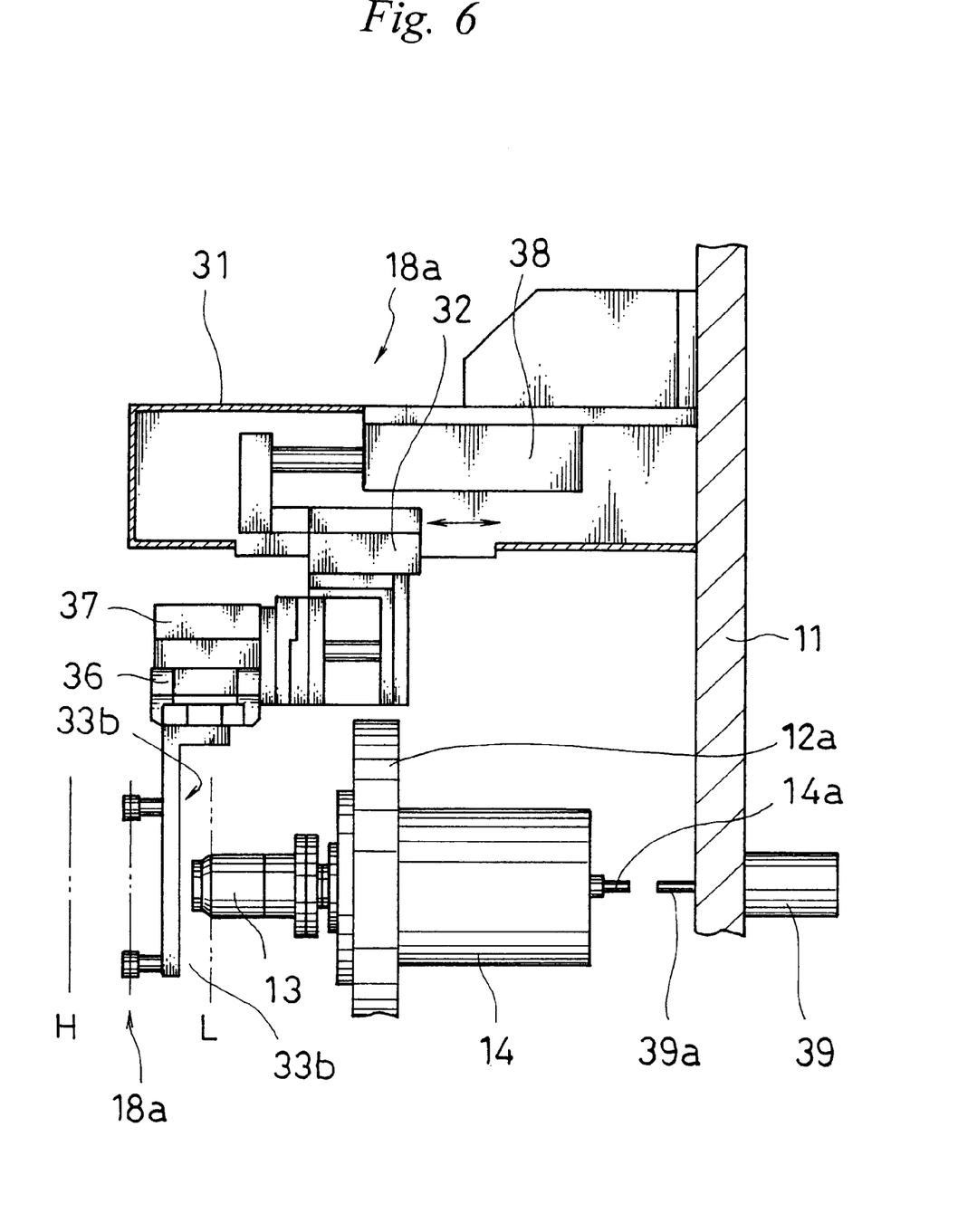
FIG. 6 is a schematic side view as viewed along arrows 6—6 in FIG. 5.

The two disks W held by the transfer hand 17a are moved to the setter hand 18a located at the loading stations. FIGS. 5 and 6 are enlarged views of the setter hand 18a.

As shown in FIGS. 5 and 6, the setter hand 18a has a drive block 31 rigidly secured to the support panel 11, which drive block 31 carries a holder 32 adapted to move back and forth horizontally and provided with fingers 33a, 33b for holding respectively a pair of disks W at the outer periphery thereof. Each of the fingers 33a, 33b has a reciprocating member 35a provided with a single roller 34 and another reciprocating member 35b provided with a pair of rollers 34, which members 35a, 35b are adapted to move closer to and away from each other along a guide member 36. The setter hand 18a is also provided with a pneumatic actuator 37 for driving the reciprocating members 35a, 35b to linearly move back and forth.

For each disk W, the related rollers 24 of the transfer hand 17a and the related rollers 34 of the setter hand 18a are displaced from each other along the circumference of the disk so that they would not interfere with each other when the disk W is passed from the transfer hand 17a to the setter hand 18a.

The fingers 33a, 33b of the setter hand 18a are driven to reciprocate between position H of the transfer hand and the loading position L of the indexing table shown in FIG. 6 by means of a pneumatic actuator 38 built in the drive block 31. Thus, the disks W brought by the transfer hand 17a to the position H of the transfer hand located vis-a-vis the setter hand 18a are then handed over to the setter hand 18a as the reciprocating members 35a, 35b of the setter hand 18a are moved away from each other and then the setter hand 18a is moved to the position H of the transfer hand. Once the disks W are handed over, the setter hand 18a is moved to the loading position L of the indexing table so that the related chucks 13 of the indexing table 12a are made to pass through the through holes of the respective disks W and engagedly hold the disks W.

Referring back to FIG. 3, an pneumatic actuator 39 is secured to the support panel 11 at a position corresponding to the loading stations A1, A2 of the indexing tables 12a, 12b, and a rod 39a to be driven to move back and forth by the actuator 39 is arranged for each chuck 13 vis-a-vis an actuator rod 13a for actuating the corresponding collet type chuck 13. The actuator rod 13a passes through the motor 14 and extends to the chuck 13. Therefore, as the rod 39a is moved forward to drive the actuator rod 13a also to move forward, the front end of the chuck 13 is radially contracted and moved out of the through hole of the disk which has been held by it. On the other hand, as the rod 39a is moved backward to drive the actuator rod 13a to move backward by the effect of a spring contained in it, the chuck is made to pass through the through hole of the disk W and engagedly hold the disk W.

Figure 7:
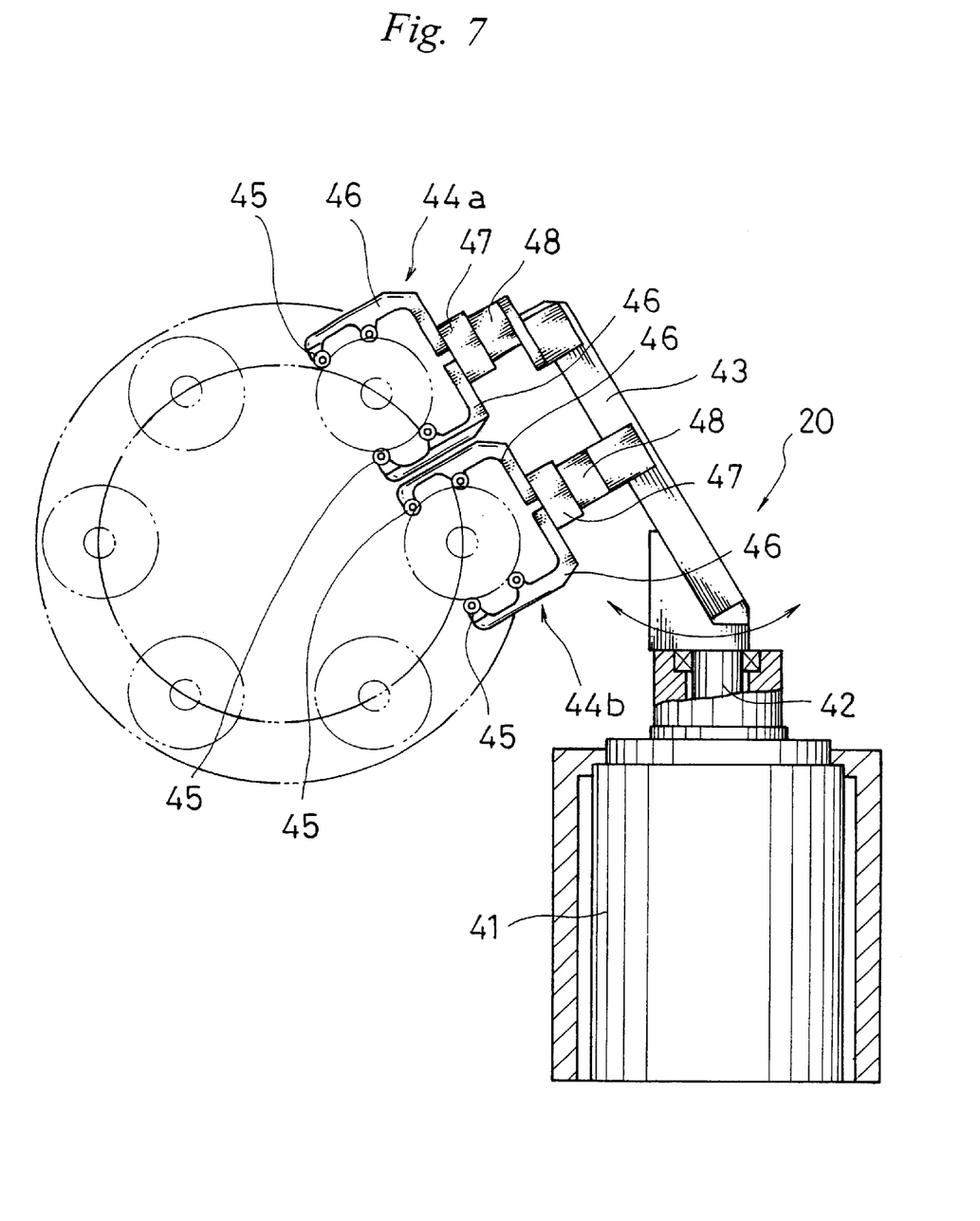
FIG. 7 is a schematic enlarged front view of the inverter hand of FIG. 1.

FIG. 7 shows the inverter hand 20 in greater detail. A holder 43 is secured to the drive shaft 42 of motor 41 secured to the support panel 11, and provided with a pair of fingers 44a, 44b for holding respectively a pair of disks W at the outer periphery thereof. Each of the fingers 44a, 44b has a pair of reciprocating members 46, each provided with a pair of rollers 45, which members 46 are adapted to move closer to and away from each other along a guide member 47. Each of the fingers 44a, 44b is also provided with a pneumatic actuator 48 for driving the reciprocating members 46 to linearly move back and forth.

Note that, while the fingers 44a, 44b of the inverter hand 20 are located respectively vis-a-vis the fingers 33a, 33b of the setter hand 18b in FIG. 1, the fingers 44a, 44b of the inverter hand 20 will be found vis-a-vis the setter hand 18c when the drive shaft 42 of the inverter hand 20 is rotated by 180°.

FIGS. 2 and 3 show the indexing table 12a of FIG. 1 in greater detail, although the other indexing table 12b has a similar configuration. FIGS. 4A and 4B show the transfer hand 17a of the charging side in detail, although the transfer hand of the discharging side is configured similarly. Likewise, each of the setter hands 18b through 18d have a configuration similar to that of the setter hand 18a shown in detail in FIGS. 5 and 6.

Figure 8:
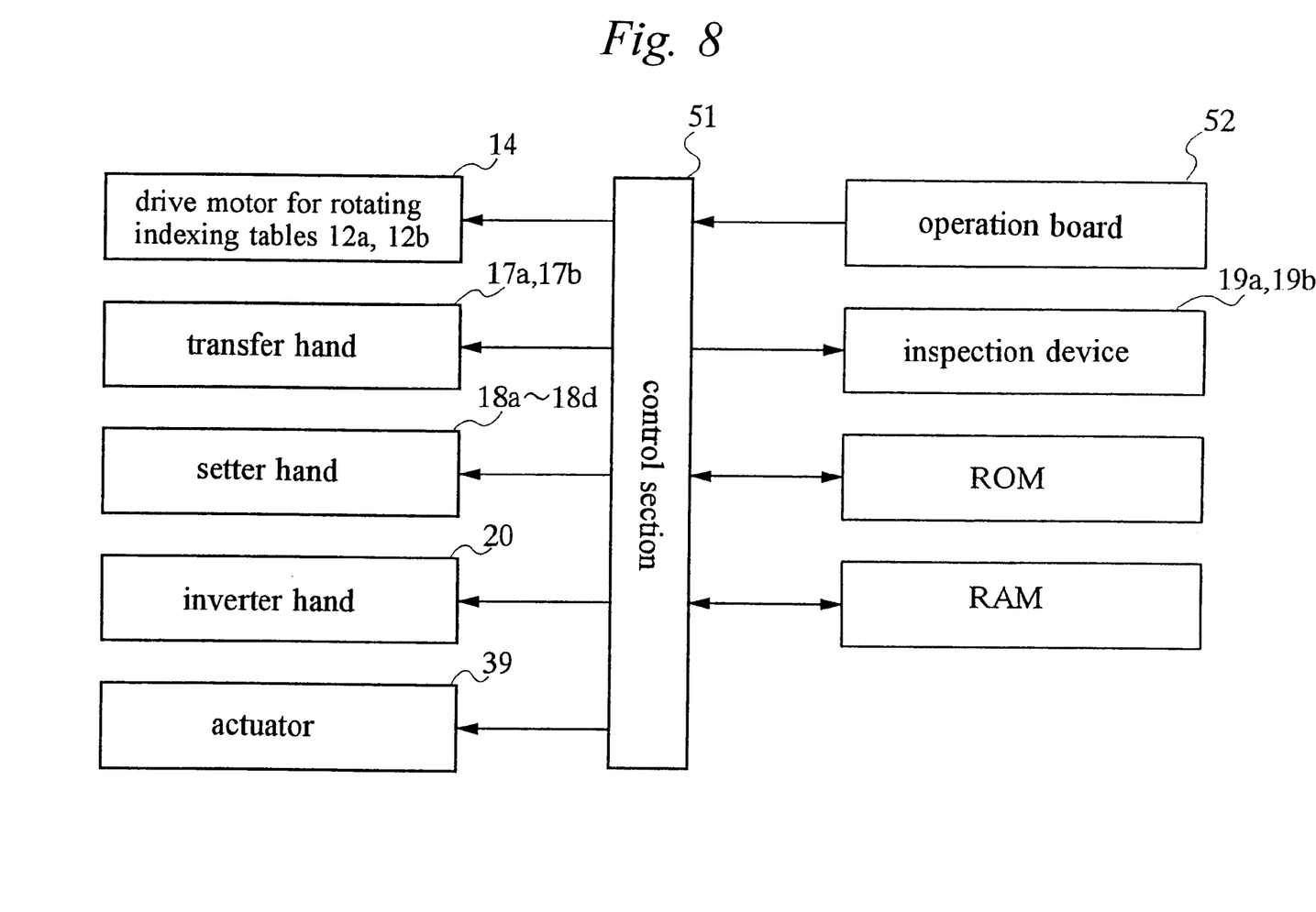
FIG. 8 is a schematic block diagram of the control unit of a surface inspection apparatus according to the invention.

FIG. 8 is a schematic block diagram of the control unit of an apparatus of surface inspection of a disk according to the invention for controlling the operation of the apparatus. Each of the components of the surface inspection apparatus is controlled for its operation by control section 51 comprising a central processing unit CPU and a ROM storing the procedure for controlling each of the components. The control section 51 is connected to an operation board for issuing commands including one for starting the operation of the surface inspection apparatus and to a display.

The procedure for inspecting the opposite surfaces of a disk W by means of the above surface inspection apparatus will be described by referring to the timing chart of FIG. 9.

A pair of disks W are moved by the transfer hand 17a to the service zone of the setter hand 18a as the disk W are held in contact with the rollers 24 at the outer periphery thereof. Under this condition, the disks W are located at position indicated by symbol H in FIG. 6. As the disks W are brought to this position, the setter hand 18a is actuated so that the disks W are handed over from the transfer hand 17a to the setter hand 18a, which is then moved backward until the chucks 13 are received in the central through holes of the respective disks W to engagedly hold the disks W. At this stage, the rods 39a of each of the actuators 39 pushes the corresponding actuator rod 13a to unlock the chuck 13 linked to it.

As the chucks 13 engagedly holding the respective disks W push the corresponding rods 39a backward by means of the actuators 39, the actuator rods 13a are moved to project from the corresponding end surfaces of the respective motors 14 under the resilient force of the related springs. Then, the collet sections of the chucks 13 radially expand to hold the respective disks W to complete the loading step. At the same time, the disks W which have been held by the setter hand 18c come to be engagedly supported by the chucks located respectively at the loading stations A1, A2 of the indexing table 12b. In FIG. 9, the time required for disks W to become loaded onto the chucks 13 respectively from the setter hands 18a, 18c is indicated by symbol T1.

As the loading step is completed, the chucks 13 at the loading stations A1, A2 are driven to rotate by the motor 14 from a standstill condition to get to a predetermined rate of revolution for inspection, e.g., 6,000 rpm. The time required for getting to the predetermined rate of revolution for inspection is T2, which is about 3 seconds in the illustrated instance. Note that, during the loading step and the step of getting to the predetermined rate of revolution, the disks W having been located at the inspection stations B1, B2 of the indexing tables 12a, 12b are revolving at the predetermined rate and being subjected to a surface inspection.

As the surface inspection of the disks W already located at the inspection stations is over, the motor 16 drives the indexing tables 12a, 12b for indexing revolution within indexing time T3, which is about 1 second in the illustrated example. By the time when the indexing tables 12a, 12b are rotated by 120°, the operation of indexing revolution is over and hence the disks W located respectively at the loading stations A1, A2 are moved to the respective inspection stations B1, B2.

The disks W brought to the inspection stations B1, B2 are already revolving at the predetermined rate of revolution for inspection so that, upon arriving at the inspection stations, they can be immediately inspected for the surface by the respective inspection devices 19a, 19b. The time required for the surface inspection, or inspection time T4, is about 7 seconds in the illustrated example. Since a pair of disks W are inspected for the surface in 7 seconds, the inspection time per disk will be 3.5 seconds.

After the end of the inspection, the disks W are moved to the respective unloading stations C1, C2 as the indexing tables 12a, 12b are driven to rotate by 120° for indexing revolution. As the disks W are moved, the motors 14 are decelerated to reduce the rate of revolution of the disks W from the rate for inspection to rate zero within time T5. The disks W now located at the unloading stations C1, C2 of the indexing table 12a and having their rate of revolution reduced to zero are handed over from the setter hand 18b to the inverter hand 20 in unloading time T6 at those stations. The surfaces of the disks W which have not been inspected are turned to face outward by the inverter hand 20 and then the disks W are handed over to the setter hand 18c of the indexing table 12b and loaded onto the table 12b at the loading stations A1, A2 of the table 12b.

Meanwhile, the disks W having been located at the unloading stations C1, C2 of the indexing table 12b are handed over to the setter hand 18d and then delivered to the outside of the surface inspection apparatus by the transfer hand 17b.

The above steps are conducted continuously to reduce the overall time required for inspecting the disks W for the surface.

With the above described surface inspection apparatus, the disks W brought to the inspection stations B1, B2 by the indexing-revolving operation of the indexing tables 12a, 12b are already revolving at the predetermined rate of revolution so that the disks W can be inspected for the surface immediately. Therefore, if compared with a conventional surface inspection apparatus, wherein disks are driven to rotate after having been brought to the respective inspection stations, the time required for them to stay at the inspection stations is reduced to about 70% to remarkably improve the efficiency of manufacturing magnetic disks on a mass production basis. Due to the fact that the disks W are made to get to a predetermined rate of revolution before the inspection starts, the disks W can take time and are not forced to get to that rate within a short period of time. The net result will be that the chucks 13 holding the discs W do not have to be tightened too hard in order to prevent any mutual sliding displacement between the disks W and the respective chucks 13 from taking place so that the peripheral surfaces of the through holes are less liable to become damaged.

Figure 9:
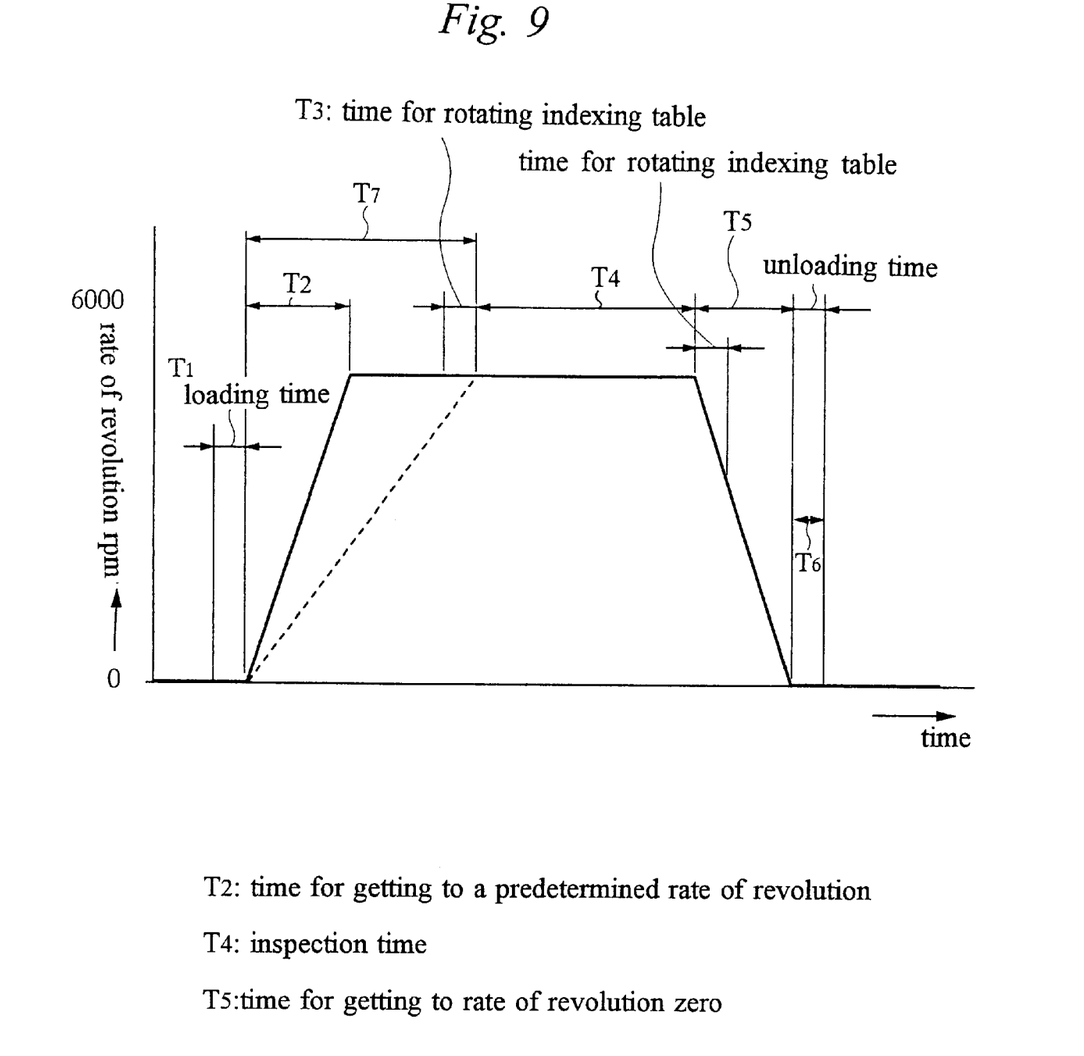
FIG. 9 is a timing chart for the operation of a surface inspection apparatus according to the invention.

While the disks W are driven to rotate from a standstill condition to get to a predetermined rate of revolution within a predetermined time T2 in the above described arrangement, they may alternatively be accelerated to get to the predetermined rate of revolution immediately before the start of inspection as indicated by a broken line and symbol T7 in FIG. 9, representing a relatively long time. Still alternatively, the disks W may not necessarily get to the predetermined rate of revolution when they arrive at the inspection stations because the rate of revolution of the can be raised further for the disks W after arriving at the inspection stations.

While the above described surface inspection apparatus comprises a pair of indexing tables so that a pair of disks are inspected for one of the opposite surfaces while another pair of disks are inspected for the other surface, it may be so arranged that a single disk is inspected for one of the opposite surfaces at a time.

Figure 10:
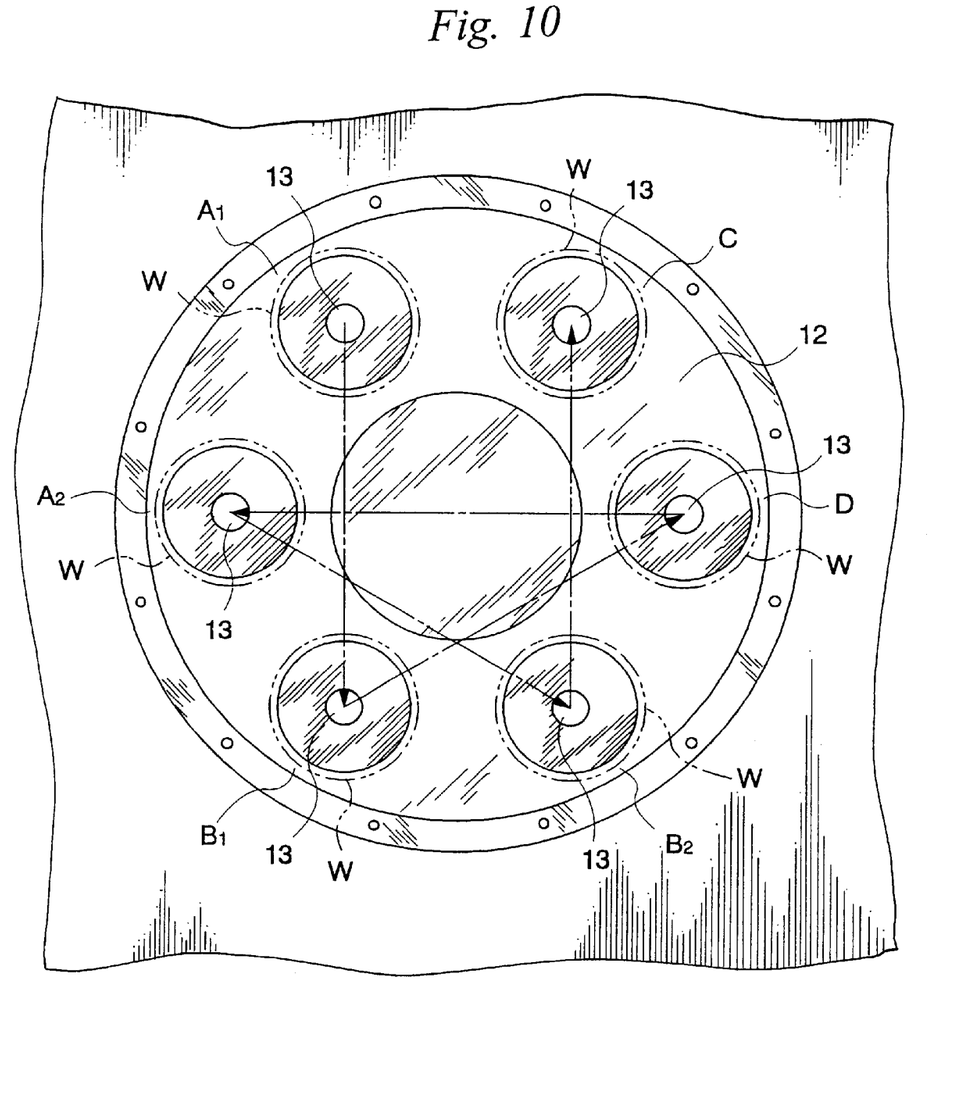
FIG. 10 is a schematic front view of the indexing table of another embodiment of surface inspection apparatus according to the invention.

FIG. 10 is a schematic front view of the indexing table 12 of another embodiment of surface inspection apparatus according to the invention and adapted to inspect works W on a one by one basis. The indexing table 12 is provided with chucks 13 arranged angularly at regular intervals of 60° as in the case of the indexing tables 12a, 12b of the above embodiment. However, with this embodiment, only a single disk W is loaded onto the chuck 13 located at the first loading station A1.

The indexing table 12 is driven to rotate by 120° at a time for indexing revolution, and the disk W at the first loading station A1 is inspected for one of the opposite surfaces at first inspection station B1. After the inspection of the first one of the surfaces, the disk W is moved to inverting station D by the indexing table 12, where it is removed from the chuck 13 by means of an inverter hand (not shown) and turned upside down while it is moved to second loading station A2 displaced by 180° from it. The disk W is loaded onto the chuck located at the second loading station A2 once again. Then, the disk W is moved to second inspection station B2 by the indexing table 12 as the table is driven to rotate by 120° for indexing revolution, where it is inspected for the other surface. When the inspection at the second inspection station B2 is over to complete the operation of inspecting the disk W for the both sides, the indexing table 12 is driven to rotate by further 120° for indexing revolution to get to unloading station C, where the disk W is delivered to the outside of the housing.

With this second embodiment of surface inspection apparatus, the disk W is driven to rotate to get to a predetermined rate of revolution between the loading station A1 or A2 and the inspection station B1 or B2, whichever appropriate.

Thus, a surface inspection apparatus according to the invention is described in detail by way of preferred embodiments, although the present invention is not limited thereto and they can be modified in various different way without departing from the scope of the invention.

For example, while each of the indexing tables of the above embodiments is provided with a total of six chucks 13 and driven to rotate by 120° each time for indexing revolution, a larger number of chucks may be arranged on the indexing table by using a table having a larger diameter. While the indexing tables 12, 12a, 12b of the above embodiments are arranged vertically, one or more than one indexing tables adapted to rotate horizontally may be used for a surface inspection apparatus according to the invention. While, in the above description, each disk is made of aluminum and subjected to a predetermined surface treatment process and subsequently the disk is inspected for the surface before forming a magnetic film on the surface, a surface inspection apparatus according to the invention may be used also to inspect the surface of a disk carrying thereon a magnetic film or the surface of a glass disk. In short, a surface inspection apparatus according to the invention can be used at various stages of manufacturing disks.

With a surface inspection apparatus according to the invention, a disk moved from a loading station to an inspection station by an indexing-revolving operation of the indexing table of the apparatus is already revolving at the predetermined rate of revolution so that it can be inspected for the surface immediately. As a result, the operation of surface inspection can be conducted highly efficiently to improve the process of manufacturing magnetic disks.

With a surface inspection apparatus according to the invention, each disk is driven to rotate to get to a predetermined rate of revolution while it is transferred to an inspection station. In other words, the next disk is driven to rotate to get to the predetermined rate of revolution in a relatively long period of time, while the preceding disk is being inspected at the inspection station. The net effect will be that the chuck holding the disc do not have to be tightened too hard in order to prevent any mutual sliding displacement between the disk and the chuck from taking place so that the peripheral surface of the through hole of the disk is less liable to become damaged and hence a high quality disk can be produced.

It is claimed:

1. A method of surface inspection of a disk adapted to move a disk from a loading station to an inspection station and then to an unloading station by indexing revolution of an indexing table having a number of chucks arranged angularly at regular intervals for respectively receiving disks by means of through holes formed in said disks respectively and holding said holes in order to inspect a surface of said disk, said method comprising:

a loading step for loading said disk onto said chuck positioned at said loading station;

a first transfer step for transferring said disk from said loading station to said inspection station by rotating said indexing table;

an inspection step for inspecting said surface of said disk moved to said inspection station while driving said disk to rotate at a predetermined rate of revolution;

a second transfer step for transferring said disk from said inspection station to said unloading station after end of inspection; and a start-up step for driving said disk to start revolving after having loaded said disk onto said chuck at said loading station and before arriving at said inspection station;

thereby inspecting said surface of said disk brought to said inspection station while revolving.

2. A method of surface inspection of a disk according to claim 1, wherein said disk is made to get to said rate of revolution for inspection in said start-up step before said disk arrives at said inspection station from said loading station.

3. A method of surface inspection of a disk according to claim 1, wherein said disk is made to get to said rate of revolution for inspection in said start-up step before said disk arrives at said inspection station from said loading station and transferred to said inspection station while maintaining said rate of revolution for inspection after getting to said rate of revolution.

4. An apparatus of surface inspection of a disk having a central through hole, said apparatus comprising:

an indexing table having a number of chucks arranged angularly at regular intervals for respectively receiving by passing through said through holes and holding said disks, said indexing table being adapted to be driven to rotate for indexing revolution in order to move said disk from a loading station to an inspection station and then to an unloading station;

rotary drive means fitted to said indexing table for driving said chucks to rotate;

loading means for loading an uninspected disk onto the chuck positioned at said loading station;

surface inspection means for inspecting a surface of said disk transferred from said loading station to said inspection station;

unloading means for unloading said disk transferred from said inspection station to said unloading station after end of inspection; and control means for driving said disk to start revolving before said disk loaded onto said chuck arrives at said inspection station from said loading station;

thereby inspecting said surface of said disk brought to said inspection station while revolving.

5. An apparatus of surface inspection of a disk according to claim 4, wherein said control means causes said disk to get to said rate of revolution for inspection before said disk arrives at said inspection station from said loading station.

6. An apparatus of surface inspection of a disk according to claim 4, wherein said control means cause said disk to get to said rate of revolution for inspection before said disk arrives at said inspection station from said loading station; and said disk got to said rate of revolution is transferred to said inspection station while maintaining said rate of revolution for inspection.

7. An apparatus of surface inspection of a disk according to claim 4, wherein said indexing table has a plurality of loading stations; a plurality of inspection stations; and a plurality of unloading stations, thereby transferring and inspecting surfaces of a plurality of disks simultaneously.

8. An apparatus of surface inspection of a disk according to claim 4, wherein a disk positioned at said loading station is transferred to said inspection station by an indexing rotary motion of said indexing table with an angle of 120° and then to said unloading station by further indexing rotary motion of said indexing table with an angle of 120°.

9. An apparatus of surface inspection of a disk according to claim 4, further comprising a pair of indexing tables provided adjacent to each other; and inverting means for inverting said disk arranged between said pair of indexing tables, thereby inspecting one of said opposite surfaces of said disk on one of said indexing tables and inspecting said other surface on said other indexing table.

10. An apparatus of surface inspection of a disk according to claim 4, further comprising inverting means for inverting said disk held to said chuck, thereby inspecting said opposite surfaces of said disk by means of said single indexing table adapted for indexing revolution.

11. An apparatus of surface inspection of a disk according to claim 10, wherein said apparatus has a first loading station for loading an unprocessed disk having opposite surfaces still uninspected; a first inspection station for inspecting one of said surfaces of said disk; an inverting station for releasing said disk having one of its surfaces inspected; a second loading station for loading said released and inverted disk; a second inspection station for inspecting said other surface of said disk; an unloading station for delivering said disk having said opposite surfaces inspected to said outside; and a total of six chucks provided on said indexing table corresponding to said six stations respectively.

* * * * *